(12) United States Patent
Han et al.

(10) Patent No.: US 10,028,702 B2
(45) Date of Patent: Jul. 24, 2018

(54) BODY-MOUNTABLE DEVICES WITH TWO LAYERS

(71) Applicant: Verily Life Sciences LLC, Mountain View, CA (US)

(72) Inventors: Jennifer Sy-En Han, Fremont, CA (US); Daniel Patrick Barrows, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 124 days.

(21) Appl. No.: 15/079,800

(22) Filed: Mar. 24, 2016

(65) Prior Publication Data

US 2016/0317090 A1 Nov. 3, 2016

Related U.S. Application Data

(60) Provisional application No. 62/155,409, filed on Apr. 30, 2015.

(51) Int. Cl.
| | |
|---|---|
| *G02C 7/08* | (2006.01) |
| *A61B 5/00* | (2006.01) |
| *A61B 5/145* | (2006.01) |
| *G02C 7/04* | (2006.01) |
| *A61B 5/1486* | (2006.01) |

(Continued)

(52) U.S. Cl.
CPC ............ *A61B 5/6821* (2013.01); *A61B 5/002* (2013.01); *A61B 5/1486* (2013.01); *A61B 5/14532* (2013.01); *B29D 11/00048* (2013.01); *B29D 11/00817* (2013.01); *G02C 7/04* (2013.01); *G02C 7/049* (2013.01); *G02C 11/10* (2013.01); *A61B 5/7445* (2013.01); *A61B 2560/0214* (2013.01); *A61B 2562/12* (2013.01); *G02C 2202/16* (2013.01)

(58) Field of Classification Search
CPC ...... G02C 2202/16; G02C 7/04; G02C 7/049; G02C 7/085
USPC .......................... 351/159.39, 159.03, 159.02
See application file for complete search history.

(56) References Cited

U.S. PATENT DOCUMENTS

| | | | |
|---|---|---|---|
| 2013/0135578 A1 | 5/2013 | Pugh et al. | |
| 2014/0268027 A1 | 9/2014 | Pugh et al. | |
| 2014/0340632 A1* | 11/2014 | Pugh ...................... | G02C 7/085 351/159.03 |

OTHER PUBLICATIONS

Mansouri, "The Road Ahead to Continuous 24-Hour Intraocular Pressure Monitoring in Glaucoma", Journal of Ophthalmic and Vision Research 2014, vol. 9, No. 2.

* cited by examiner

*Primary Examiner* — Hung Dang
(74) *Attorney, Agent, or Firm* — McDonnell Boehnen Hulbert & Berghoff LLP

(57) ABSTRACT

A body-mountable device may include a first layer, a second layer, and an electronic structure. The first layer may include a first topographical feature, while the second layer may include a second topographical feature. The first topographical feature and the second topographical feature may be reciprocally-shaped. The second layer may be mounted on the first layer such that the first topographical feature interfaces with the second topographical feature, thereby mechanically securing the second layer to the first layer. The electronic structure, which may include an antenna, a sensor, and an electronic device, may be embedded in the second layer. In an example in which the body-mountable device is an eye-mountable device, the first layer may be a posterior lens, and the second layer may be an anterior lens.

20 Claims, 7 Drawing Sheets

(51) Int. Cl.
*G02C 11/00* (2006.01)
*B29D 11/00* (2006.01)

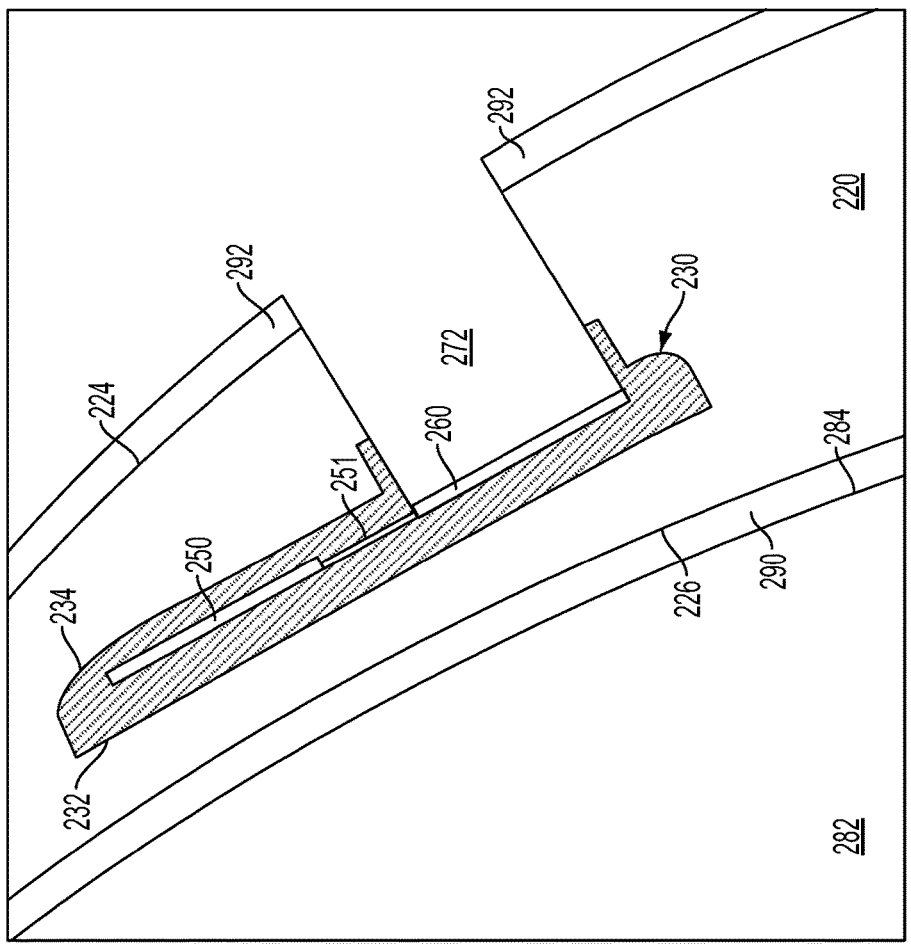
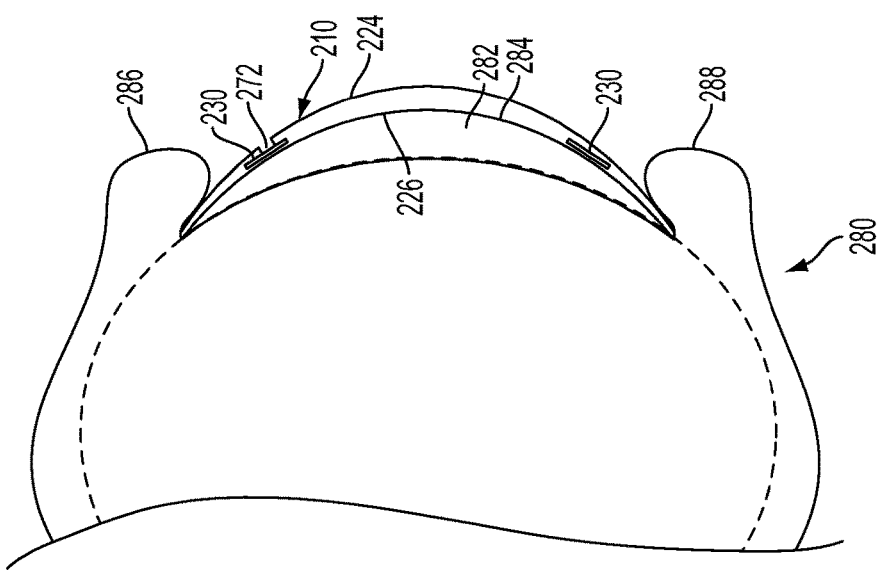
FIG. 2d
FIG. 2c

US 10,028,702 B2

BODY-MOUNTABLE DEVICES WITH TWO LAYERS

CROSS-REFERENCE TO RELATED APPLICATION

This application claims priority to U.S. Provisional Patent Application No. 62/155,409, filed Apr. 30, 2015, which is incorporated herein by reference.

BACKGROUND

Unless otherwise indicated herein, the materials described in this section are not prior art to the claims in this application and are not admitted to be prior art by inclusion in this section.

A body-mountable device may be configured to monitor health-related information based on at least one analyte from a user. For example, a bio-compatible device may be embedded in a polymer to provide the body-mountable device. The bio-compatible device includes a sensor configured to detect the at least one analyte (e.g., glucose) in a fluid of a user wearing the body-mountable device. The body-mountable device may also be configured to monitor various other types of health-related information.

SUMMARY

In one aspect, a method is disclosed. The method includes forming a first lens that has a first topographical feature. The method also includes forming a second lens that has a second topographical feature, with the first topographical feature and the second topographical feature having reciprocal shapes. Embedded in the second lens is an electronic structure that comprises an antenna, a sensor, and an electronic device. The method further includes mounting the second lens on the first lens such that first topographical feature interfaces with the second topographical feature, thereby mechanically securing the second lens to the first lens.

In another aspect, a body-mountable device is disclosed. The body-mountable device comprises a first lens having a first topographical feature. The body-mountable device also comprises a second lens having a second topographical feature, with the first topographical feature and the second topographical feature having reciprocal shapes. The second lens is mounted on the first lens such that the first topographical features interfaces with the second topographical feature, thereby mechanically securing the second lens to the first lens. The eye-mountable device further includes an electronic structure comprising an antenna, a sensor, and an electronic device, the electronic device being embedded in the second lens In yet another aspect, a system is disclosed. The system includes means for forming a first lens that has a first topographical feature. The system also includes means for forming a second lens that has a second topographical feature, with the first topographical feature and the second topographical feature having reciprocal shapes. The system may further include means for eembedding in the second lens an electronic structure that comprises an antenna, a sensor, and an electronic device. Additionally, the system includes means for mounting the second lens on the first lens such that first topographical feature interfaces with the second topographical feature, thereby mechanically securing the second lens to the first lens.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2c is a side cross-section view of the eye-mountable device of FIG. 2a while mounted to a corneal surface of the eye, according to an example embodiment.

FIG. 2d is a side cross-section view showing the tear film layers surrounding the surfaces of the eye-mountable device mounted as shown in FIG. 2c, according to an example embodiment.

DETAILED DESCRIPTION

Figure 1:
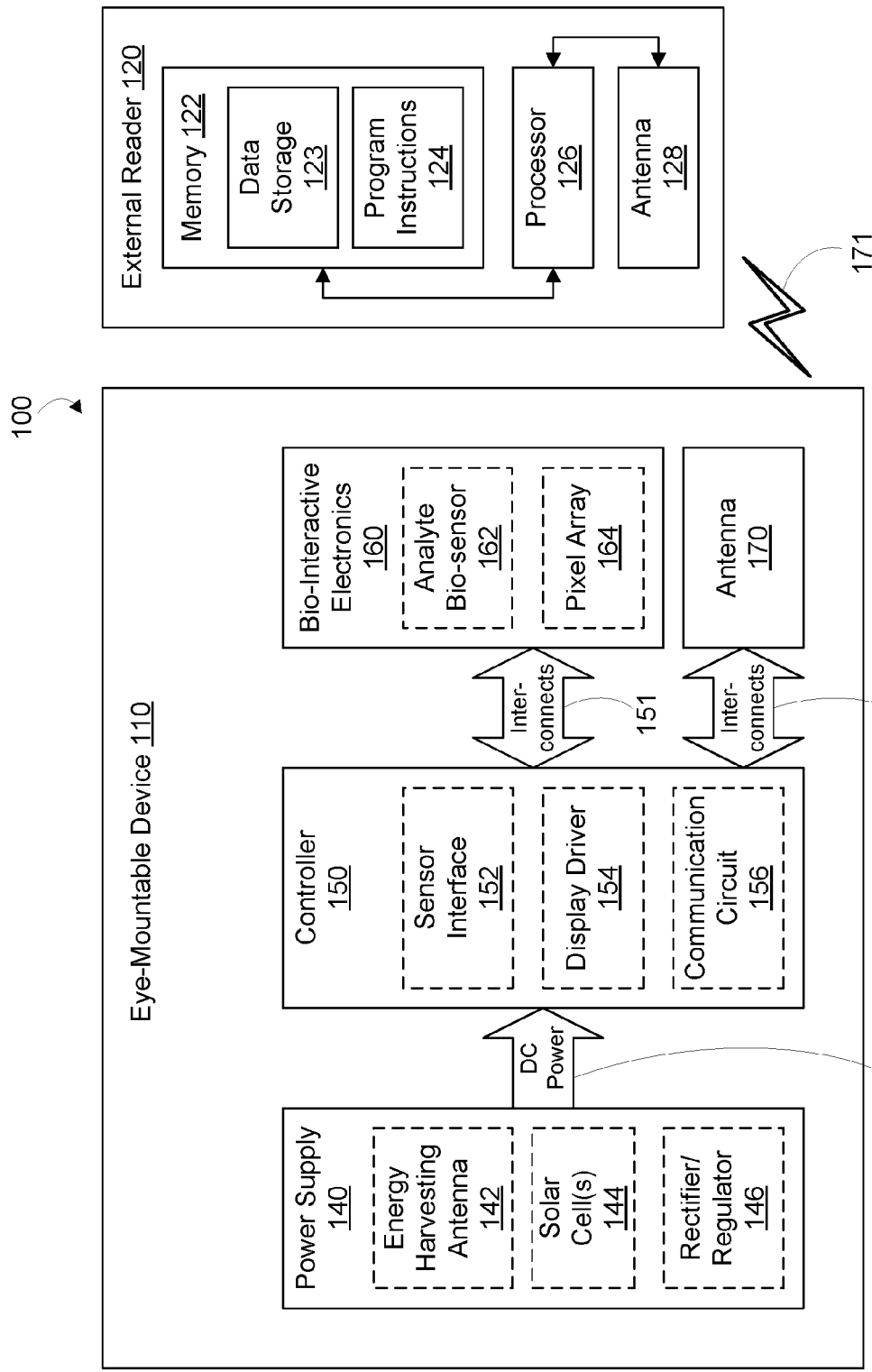
FIG. 1 is a block diagram of a system with a body-mountable device in wireless communication with an external reader, according to an example embodiment.

The following detailed description describes various features and functions of the disclosed methods and systems with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

I. INTRODUCTION

A body-mountable device may include an electronic structure embedded in a transparent polymer. The electronic structure may include at least one antenna, a sensor, and an electronic device. In an example embodiment, the body-mountable device may be an eye-mountable device formed to have the same general shape as a contact lens, thereby allowing the user to mounting the eye-mountable device to the user's cornea. During use, the electronic structure may measure an analyte in a tear film of a user and transmit information indicative of the analyte measurement to another device, such as a smartphone or other computing system.

To allow for use in a lens-shaped eye-mountable device, the electronic structure may have a ring shape. In order to maintain the shape of the eye-mountable device, the transparent polymer may include one or more bio-compatible materials that provide enough rigidity to maintain the shape of the eye-mountable device (e.g., the transparent polymer should provide enough structure to resist deformations in the shape of the electronic structure) while also being flexible enough for use as a contact lens. One example of such a material is silicone elastomer. Silicone elastomer is also hydrophobic, which may allow for more accurate measurements of analytes in the user's tear film. But because silicone elastomer is hydrophobic, silicone elastomer lenses tend to bind to the cornea, thereby resulting in the posterior surface of the lens tightening on the eye and causing discomfort.

Embodiments described herein relate to body-mountable devices, particularly (though not exclusively) eye-mountable devices, and to methods for fabricating such body-mountable devices. More specifically, eye-mountable devices described herein may be formed from two transparent lenses: a posterior lens and anterior lens. Whereas the anterior lens, in which the electronic structure is embedded, may be formed of a stiffer, hydrophobic bio-compatible material, the posterior lens—which will directly contact the cornea during use—may comprise a hydrophilic bio-compatible material that is less susceptible to corneal binding, and thus more tolerable to wear than the material of the anterior lens. As one example, the anterior lens may include a silicone elastomer, and the posterior lens may include a silicone hydrogel. In this manner, the eye-mountable devices disclosed herein may be more comfortable for a user to wear, thereby promoting use of the eye-mountable device.

To facilitate proper alignment and securement of the anterior lens to the posterior lens, the posterior lens and the anterior lens may have reciprocal topographical features on respective mating surfaces. As one example, the anterior lens may include a protrusion on a posterior surface, while the posterior lens may include a reciprocally-shaped depression on an anterior surface. A diameter of the depression may be the same as or slightly smaller than a diameter of the protrusion (i.e., within several tenths of a millimeter). When mounting the posterior lens to the anterior lens, the depression may be aligned over the protrusion, and a compressive force may be applied to press the posterior lens onto the anterior lens. The protrusion may enter the depression, and the resulting interface between the protrusion and the depression may mechanically secure the anterior lens to the posterior lens.

II. EXAMPLE SYSTEMS AND DEVICES

One type of body-mountable device—an eye-mountable device that is configured to detect at least one analyte in a tear film of a user wearing the eye-mountable device—will now be described in greater detail.

FIG. 1 is a block diagram of a system 100 that includes an eye-mountable device 110 in wireless communication with an external reader 120. The eye-mountable device 110 may be a polymeric material that may be appropriately shaped for mounting to a corneal surface and in which a structure is at least partially embedded. The structure may include a power supply 140, a controller 150, bio-interactive electronics 160, and an antenna 170.

In some embodiments, the structure may be a bio-compatible device in which some or all of the components formed or mounted thereon are encapsulated by a bio-compatible material.

In some example embodiments, the structure may be positioned away from the center of the eye-mountable device 110 and thereby avoid interference with light transmission to the central, light-sensitive region of the eye. For example, where the eye-mountable device 110 is shaped as a curved disk, the structure may be embedded around the periphery (e.g., near the outer circumference) of the disk. In other example embodiments, the structure may be positioned in or near the central region of the eye-mountable device 110. For example, portions of the structure may be substantially transparent to incoming visible light to mitigate interference with light transmission to the eye. Moreover, in some embodiments, the bio-interactive electronics 160 may include a pixel array 164 that emits and/or transmits light to be received by the eye according to display instructions. Thus, the bio-interactive electronics 160 may optionally be positioned in the center of the eye-mountable device so as to generate visual cues perceivable to a wearer of the eye-mountable device 110, such as displaying information (e.g., characters, symbols, flashing patterns, etc.) on the pixel array 164.

The power supply 140 is configured to harvest ambient energy to power the controller 150 and bio-interactive electronics 160, and may include an energy harvesting antenna 142 and/or solar cells 144. The energy harvesting antenna 142 may capture energy from incident radio radiation. The solar cells 144 may comprise photovoltaic cells configured to capture energy from incoming ultraviolet, visible, and/or infrared radiation.

A rectifier/regulator 146 may be used to condition the captured energy to a stable DC supply voltage 141 at a level suitable for operating the controller, and then supply the voltage to the controller 150. The rectifier/regulator 146 may include one or more energy storage devices to mitigate high frequency variations in the energy harvesting antenna 142 and/or solar cell(s) 144. For example, one or more energy storage devices (e.g., a capacitor or an inductor) may be connected in parallel across the outputs of the rectifier/regulator 146 to regulate the DC supply voltage 141 and may be configured to function as a low-pass filter.

The controller 150 is configured to execute instructions to operate the bio-interactive electronics 160 and the antenna 170. The controller 150 includes logic circuitry configured to operate the bio-interactive electronics 160 so as to interact with a biological environment of the eye-mountable device 110. The interaction could involve the use of one or more components, such an analyte bio-sensor 162 in the bio-interactive electronics 160, to obtain input from the biological environment. Additionally or alternatively, the interaction could involve the use of one or more components, such as a pixel array 164, to provide an output to the biological environment.

In one example, the controller 150 includes a sensor interface module 152 that is configured to operate the analyte bio-sensor 162. The analyte bio-sensor 162 may be, for example, an amperometric electrochemical sensor that includes a working electrode and a reference electrode driven by a sensor interface. A voltage is applied between the working and reference electrodes to cause an analyte to undergo an electrochemical reaction (e.g., a reduction and/or oxidation reaction) at the working electrode. The electrochemical reaction generates an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent may also be included to sensitize the electrochemical sensor to one or more desired analytes. For example, a layer of glucose oxidase ("GOX") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

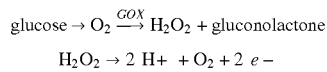

$$H_2O_2 \rightarrow 2\ H+ +O_2 +2\ e-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 may also include a display driver module 154 for operating a pixel array 164. The pixel array 164 is an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 may also include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 may also include a communication circuit 156 for sending and/or receiving information via the antenna 170. The communication circuit 156 may include one or more oscillators, mixers, frequency injectors, or the like to modulate and/or demodulate information on a carrier frequency to be transmitted and/or received by the antenna 170. In some example embodiments, the eye-mountable device 110 is configured to indicate an output from a bio-sensor by modulating an impedance of the antenna 170 in a manner that is perceivable by the external reader 120. For example, the communication circuit 156 can cause variations in the amplitude, phase, and/or frequency of backscatter radiation from the antenna 170, and such variations may then be detected by the reader 120.

The controller 150 is connected to the bio-interactive electronics 160 via interconnects 151. Similarly, the controller 150 is connected to the antenna 170 via interconnects 157. The interconnects 151, 157 may comprise a patterned conductive material (e.g., gold, platinum, palladium, titanium, copper, aluminum, silver, metals, any combinations of these, etc.).

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component.

Additionally or alternatively, the energy harvesting antenna 142 and the antenna 170 can be implemented in the same, dual-purpose antenna. For example, a loop antenna can both harvest incident radiation for power generation and communicate information via backscatter radiation.

The external reader 120 includes an antenna 128 (or group of more than one antennae) to send and receive wireless signals 171 to and from the eye-mountable device 110. The external reader 120 also includes a computing system with a processor 126 in communication with a memory 122. The memory 122 is a non-transitory computer-readable medium that can include, without limitation, magnetic disks, optical disks, organic memory, and/or any other volatile (e.g., RAM) or non-volatile (e.g., ROM) storage system readable by the processor 126. The memory 122 includes a data storage 123 to store indications of data, such as sensor readings (e.g., from the analyte bio-sensor 162), program settings (e.g., to adjust behavior of the eye-mountable device 110 and/or external reader 120), etc. The memory 122 also includes program instructions 124 for execution by the processor 126. For example, the program instructions 124 may cause the external reader 120 to provide a user interface that allows for retrieving information communicated from the eye-mountable device 110 (e.g., sensor outputs from the analyte bio-sensor 162). The external reader 120 may also include one or more hardware components for operating the antenna 128 to send and receive the wireless signals 171 to and from the eye-mountable device 110. For example, oscillators, frequency injectors, encoders, decoders, amplifiers, and filters can drive the antenna 128 according to instructions from the processor 126.

The external reader 120 may be a smart phone, digital assistant, or other portable computing device with wireless connectivity sufficient to provide the wireless communication link 171. The external reader 120 may also be implemented as an antenna module that can be plugged in to a portable computing device, such as in an example where the communication link 171 operates at carrier frequencies not commonly employed in portable computing devices. In some instances, the external reader 120 is a special-purpose device configured to be worn relatively near a wearer's eye to allow the wireless communication link 171 to operate using little or low power. For example, the external reader 120 can be integrated in a piece of jewelry such as a necklace, earing, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. To perform a reading with the system 100 configured as a tear film analyte monitor, the external reader 120 can emit radio frequency radiation 171 that is harvested to power the eye-mountable device 110 via the power supply 140. Radio frequency electrical signals captured by the energy harvesting antenna 142 (and/or the antenna 170) are rectified and/or regulated in the rectifier/regulator 146 and a regulated DC supply voltage 141 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 120 (e.g., via the communication circuit 156).

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 120 to the eye-mountable device 110 to request a measurement. By periodically interrogating the eye-mountable device 110 (e.g., by supplying radio frequency radiation 171 to temporarily turn the device on) and storing the sensor results (e.g., via the data storage 123), the external reader 120 can accumulate a set of analyte concentration measurements over time without continuously powering the eye-mountable device 110.

Figure 2A:
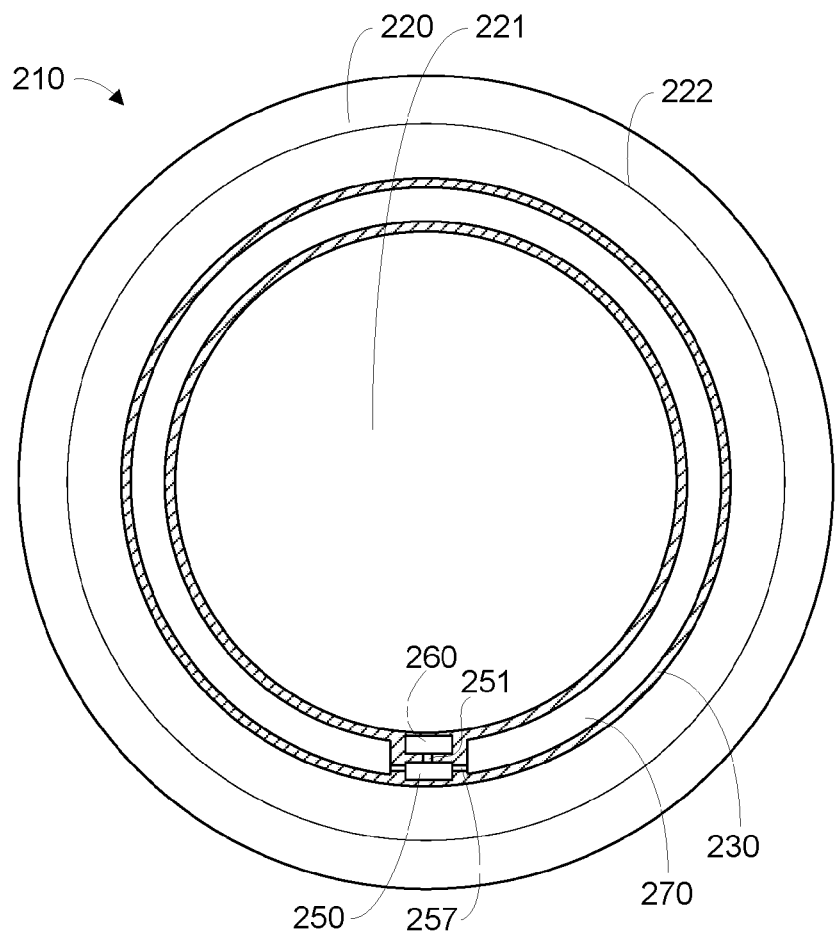
FIG. 2a is a top view of an eye-mountable device, according to an example embodiment.
Figure 2B:
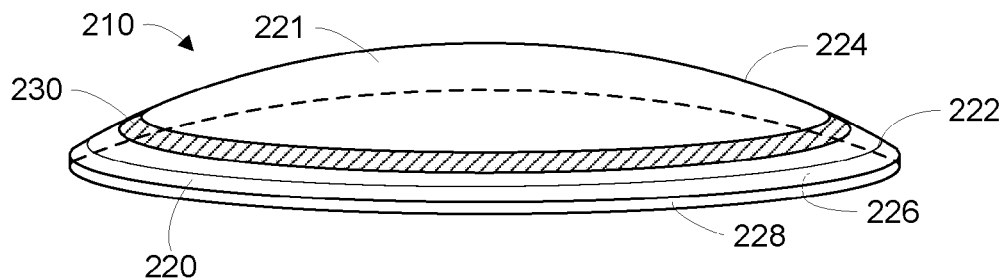
FIG. 2b is a side view of an eye-mountable device, according to an example embodiment.

FIG. 2a is a top view of an eye-mountable device 210. FIG. 2b is side view of the eye-mountable device 210. It is noted that relative dimensions in FIGS. 2a and 2b are not necessarily to scale, but have been rendered for purposes of explanation only in describing the arrangement of the eye-mountable device 210.

In line with the above discussion, the eye-mountable device 210 may include an posterior lens 220 and an anterior lens 221, each of which may be formed from a substantially transparent, bio-compatible polymeric material to allow incident light to be transmitted to the eye. In practice, the eye-mountable device 210 may appear as one lens. For illustrative purposes, an edge 222 of the anterior lens 221 is shown in FIGS. 2a and 2b to distinguish the posterior lens 220 from the anterior lens 221

In some examples, the posterior lens 220 and the anterior lens 221 may include different polymeric materials. By way of example, the posterior lens 220 may include a hydrophilic polymeric material that promotes maintaining moisture on the corneal surface, such as a silicone hydrogel, while the anterior lens 221 may include a stiffer, hydrophobic material that is promotes sensor operation, such as a silicone elastomer. In other examples, the posterior lens 220 may include a silicone hydrogel while the anterior lens 221 may include a different hydrogel. Alternatively, both the posterior lens 220 and the anterior lens 221 may include the same polymeric material, such as a silicone hydrogel.

To facilitate contact-mounting, the posterior lens 220 may comprise a concave posterior surface 226 configured to adhere ("mount") to a moistened corneal surface (e.g., by capillary forces with a tear film coating the corneal surface). While mounted with the posterior surface 226 against the eye, an anterior surface 224 of eye-mountable device 210, which may be defined by the anterior surface of the anterior lens 221 and a portion of the anterior surface of the posterior lens 220, is formed so as not to interfere with eye-lid motion while the eye-mountable device 210 is mounted to the eye. A circular outer side edge 228 connects the anterior surface 224 and the posterior surface 226. The "top" view shown in FIG. 2a is facing the anterior surface 224.

The eye-mountable device 210 can have dimensions similar to a vision correction and/or cosmetic contact lenses, such as a diameter of about 13.5 millimeters to about 14.5 millimeters, and a thickness of about 0.1 millimeters to about 0.5 millimeters. However, the diameter and thickness values are provided for explanatory purposes only. In some embodiments, the dimensions of the eye-mountable device 210 may be selected according to the size and/or shape of the corneal surface and/or the scleral surface of the wearer's eye. In other embodiments, the eye-mountable device 210 is shaped to provide a predetermined, vision-correcting optical power, such as provided by a prescription contact lens.

An electronic structure 230 is embedded in the eye-mountable device 210. The electronic structure 230 may be embedded to be situated near the edge 222 of the anterior lens 221. Such a position ensures that the electronic structure 230 will not interfere with a wearer's vision when the eye-mountable device 210 is mounted on a wearer's eye, because it is positioned away from a central region of the anterior lens 221 where incident light is transmitted to the light-sensing portions of the eye. Moreover, portions of the electronic structure 230 can be formed of a transparent material to further mitigate effects on visual perception.

The electronic structure 230 may be shaped as a flat, circular ring (e.g., a disk with a centered hole). The flat surface of the electronic structure 230 (e.g., along the radial width) allows for mounting electronics such as chips (e.g., via flip-chip mounting) and for patterning conductive materials to form electrodes, antenna(e), and/or interconnections. The electronic structure 230 and the anterior lens 221 may be approximately cylindrically symmetric about a common central axis. The electronic structure 230 may have, for example, a diameter of about 10 millimeters, a radial width of about 1 millimeter (e.g., an outer radius 1 millimeter greater than an inner radius), and a thickness of about 50 micrometers. These dimensions are provided for example purposes only, and in no way limit this disclosure.

A loop antenna 270, controller 250, and bio-interactive electronics 260 are included in the electronic structure 230. The controller 250 may be a chip including logic elements configured to operate the bio-interactive electronics 260 and the loop antenna 270. The controller 250 is electrically connected to the loop antenna 270 by interconnects 257 also situated on the electronic structure 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) may be formed from any type of conductive material and may be patterned by any process that can be used for patterning such materials, such as deposition or photolithography, for example. The conductive materials patterned on the electronic structure 230 may be, for example, gold, platinum, palladium, titanium, carbon, aluminum, copper, silver, silver-chloride, conductors formed from noble materials, metals, or any combinations of these materials. Other materials may also be envisioned.

The electronic structure 230 may be a bio-compatible device in which some or all of the components are encapsulated by a bio-compatible material. In one example, the controller 250, interconnects 251, 257, bio-interactive electronics 260, and the loop antenna 270 are fully encapsulated by bio-compatible material, except for the sensor electrodes in the bio-interactive electronics 260.

As shown in FIG. 2a, the bio-interactive electronics module 260 is on a side of the electronic structure 230 facing the anterior surface 224. Where the bio-interactive electronics module 260 includes an analyte bio-sensor, for example, mounting such a bio-sensor on the electronic structure 230 to be close to the anterior surface 224 allows the bio-sensor to sense analyte that has diffused through anterior surface 224 or has reached the bio-sensor through a channel in the anterior surface 224 (FIGS. 2c and 2d show a channel 272).

The loop antenna 270 is a layer of conductive material patterned along the flat surface of the electronic structure 230 to form a flat conductive ring. In some example embodiments, the loop antenna 270 does not form a complete loop. For example, the loop antenna 270 may include a cutout to allow room for the controller 250 and bio-interactive electronics 260, as illustrated in FIG. 2a. However, in another example embodiment, the loop antenna 270 can be arranged as a continuous strip of conductive material that wraps entirely around the electronic structure 230 one or more times. Interconnects between the ends of such a wound antenna (e.g., the antenna leads) can connect to the controller 250 in the electronic structure 230. In some embodiments, the loop antenna can include a plurality of conductive loops spaced apart from each other, such as three conductive loops, five conductive loops, nine conductive loops, etc. With such an arrangement, the polymeric material 220 may extend between adjacent conductive loops in the plurality of conductive loops.

FIG. 2c is a side cross-section view of the eye-mountable electronic device 210 mounted to a corneal surface 284 of an eye 280. FIG. 2d is an enlarged partial view of the cross-section of the eye-mountable device shown in FIG. 2c. It is noted that relative dimensions in FIGS. 2c and 2d are not necessarily to scale, but have been rendered for purposes of explanation only in describing the arrangement of the eye-mountable device 210. Some aspects are exaggerated to allow for illustration and to facilitate explanation.

The eye 280 includes a cornea 282 that is covered by bringing an upper eyelid 286 and a lower eyelid 288 together over the surface of the eye 280. Incident light is received by the eye 280 through the cornea 282, where light is optically directed to light sensing elements of the eye 280 to stimulate visual perception. The motion of the upper and lower eyelids 286, 288 distributes a tear film across the exposed corneal surface 284 of the eye 280. The tear film is an aqueous solution secreted by the lacrimal gland to protect and lubricate the eye 280. When the eye-mountable device 210 is mounted in the eye 280, the tear film coats both the anterior and posterior surfaces 224, 226, providing an inner layer 290 (along the posterior surface 226) and an outer layer 292 (along the anterior surface 224). The inner layer 290 on the corneal surface 284 also facilitates mounting the eye-mountable device 210 by capillary forces between the posterior surface 226 and the corneal surface 284. In some embodiments, the eye-mountable device 210 can also be held over the eye 280 in part by vacuum forces against the corneal surface 284 due to the curvature of the posterior surface 226. The tear film layers 290, 292 may be about 10 micrometers in thickness and together account for about 10 microliters of fluid.

The tear film is in contact with the blood supply through capillaries in the structure of the eye and includes many biomarkers found in blood that are analyzed to diagnose health states of an individual. For example, tear film includes glucose, calcium, sodium, cholesterol, potassium, other biomarkers, etc. The biomarker concentrations in tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body.

As shown in the cross-sectional views in FIGS. 2c and 2d, the electronic structure 230 can be inclined so as to be approximately parallel to the adjacent portion of the anterior surface 224. As described above, the electronic structure 230 is a flattened ring with an inward-facing surface 232 (closer to the posterior surface 226 of the polymeric material 220) and an outward-facing surface 234 (closer to the anterior surface 224). The electronic structure 230 can include electronic components and/or patterned conductive materials adjacent to either or both surfaces 232, 234.

As shown in FIG. 2d, the bio-interactive electronics 260, the controller 250, and the conductive interconnect 251 are located between the outward-facing surface 234 and the inward-facing surface 632 such that the bio-interactive electronics 260 are facing the anterior surface 224. With this arrangement, the bio-interactive electronics 260 can receive analyte concentrations in the tear film 292 through the channel 272. However, in other examples, the bio-interactive electronics 260 may be mounted on the inward-facing surface 232 of the electronic structure 230 such that the bio-interactive electronics 260 are facing the posterior surface 226.

While the body-mountable device has been described as comprising the eye-mountable device 110 and/or the eye-mountable device 210, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 110 and/or the eye-mountable device 210. For instance, the tooth-mountable device could include a polymeric material that is the same as or similar to any of the polymeric materials described herein and a structure that is the same as or similar to any of the structures described herein. With such an arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 110 and/or the eye-mountable device 210. For instance, the skin-mountable device could include a polymeric material that is the same as or similar to any of the polymeric materials described herein and a structure that is the same as or similar to any of the structures described herein. With such an arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. EXAMPLE METHODS

Figure 3:
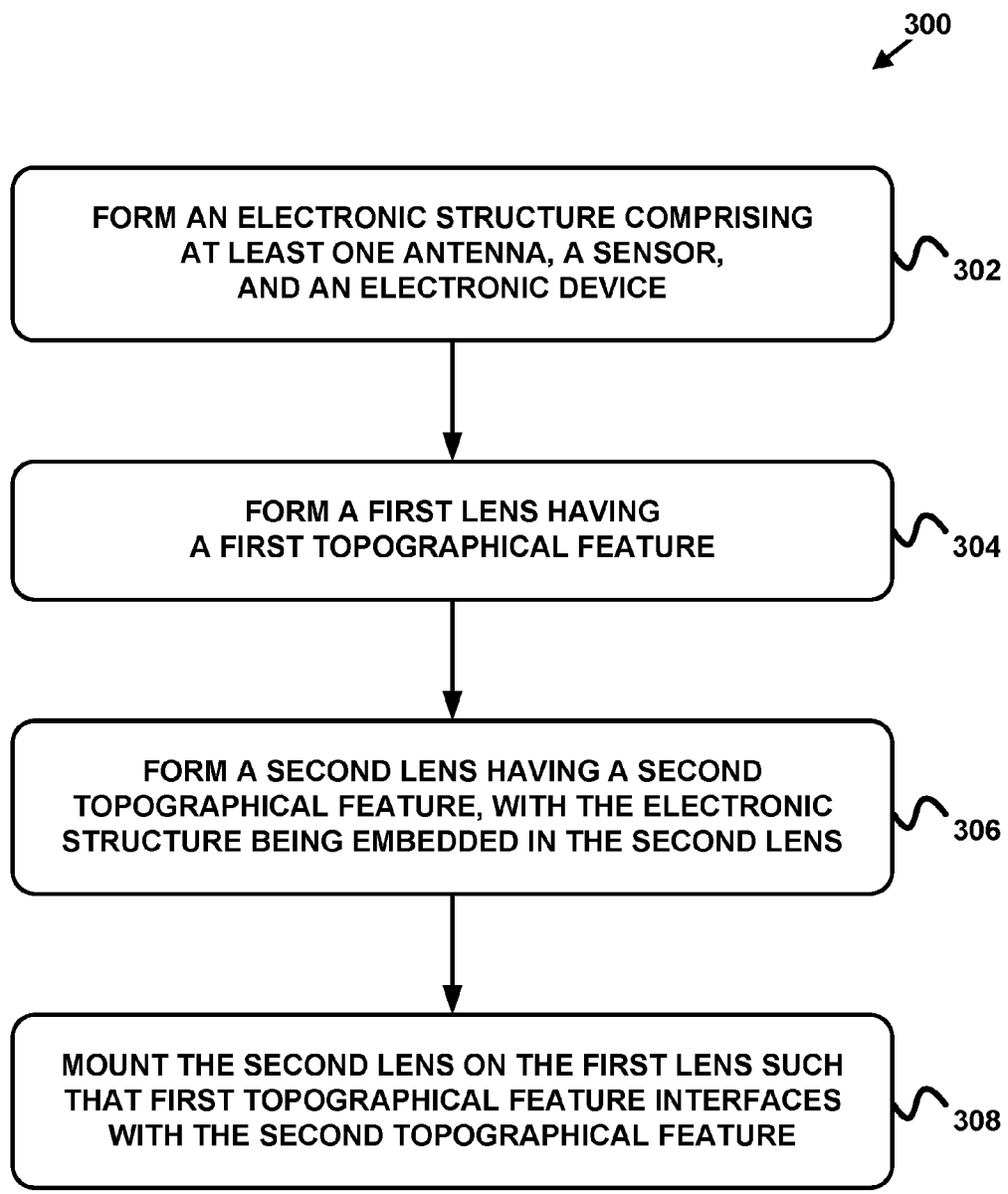
FIG. 3 is a flow chart illustrating a method for fabricating a bio-compatible device, according to an example embodiment.

FIG. 3 is a flowchart of a method 300 for fabricating an eye-mountable device, according to an example embodiment. The method 300 may involve forming an electronic structure comprising at least one antenna, a sensor, and an electronic device (block 302). The electronic structure, such as the electronic structure 230 depicted in FIGS. 2a-2d, may be formed using any suitable method or process now known or later developed.

The method 300 may also involve forming a first lens having a first topographical feature (block 304) and a second lens having a second topographical feature (block 306). For illustrative purposes, the first lens is a posterior lens of the eye-mountable device (e.g., the posterior lens 220 described with respect to FIGS. 2a-2d), and the second lens is an anterior lens of the eye-mountable device (e.g., the anterior lens 221 described with respect to FIGS. 2a-2d).

Each of the first lens and the second lens may be formed using cast molding. The molds used to form the first lens may have shapes that result in the first lens having the first topographical feature on an anterior surface and a concave posterior surface. The radius of curvature of the posterior surface may be similar to the radius of curvature of a human cornea, which will subsequently facilitate mounting the eye-mountable device on the user's eye. The molds used to form the second lens, in turn, may have shapes that result in the second lens have the second topographical feature on the posterior surface and a convex anterior surface. The radius of curvature of the anterior surface may be selected so as to provide the requisite vision-correction factor for the user of the eye-mountable device.

With respect to forming the second lens, the cast molding technique may include forming the second lens in layers to facilitate embedding the electronic structure in the second lens. For instance, a first layer of the second lens may be formed, the electronic structure may be placed on the first layer, and then a second layer of the second lens may then be formed over the first layer and the electronic device so as to provide the second lens. Other examples for embedding the electronic structure in the second lens are also possible.

The first lens may have a diameter between about 13.5 millimeters and about 14.5 millimeters and a thickness between about 120 microns and about 150 microns, while the second lens may have a diameter between about 13 millimeters and about 13.3 millimeters and a thickness of about 200 microns.

In some embodiments, the first lens and the second lens may comprise different bio-compatible, transparent polymeric materials. By way of example, the first lens may comprise a hydrophilic compound suitable for maintaining a moist interface between the first lens and the user's cornea. In contrast, the second lens may comprise a hydrophobic material, which may promote better operation of the sensor included in the electronic structure. For instance, the first lens may comprise silicone hydrogel, and the second lens may comprise silicone elastomer. Alternatively, the second lens may comprise a different hydrogel (e.g., a hydrogel other than silicone hydrogel). And in yet other embodiments, both lenses may comprise silicone hydrogel.

The method 300 may further involve mounting the second lens on the first lens such that the first topographical feature interfaces with the second topographical feature (block 308), thereby mechanically securing the second lens to the first lens. Mounting the second lens on the first lens may involve aligning the second lens over the first lens such that the second topographical feature is aligned over the first topographical feature. A compressive force may then be applied to cause the first topographical feature to interface with the second topographical feature, mechanically securing the second lens to the first lens.

Additionally or alternatively, one of the first lens or the second lens may be heated prior to mounting the second lens on the first lens, thereby causing one of the first topographical feature or the second topographical feature to expand. After the second lens is mounted on the first lens, the resulting eye-mountable device may cool, and the expanded first topographical feature or second topographical feature may contract. This contraction may result in a tighter interface between the first topographical feature and the second topographical, thereby mechanically securing the first lens to the second lens.

Additionally, the heated lens (one of the first lens or the second lens) may have a tackiness that also promotes adhesion of the second lens to the first lens. In yet another example, mounting the second lens on the first lens may involve applying a transparent, bio-compatible adhesive to the first lens and/or the second lens. The adhesive may further secure the second lens to the first lens. The adhesive may comprise any material or combination of materials now known or later developed that is suitable for use in an eye-mountable device.

Figure 4:
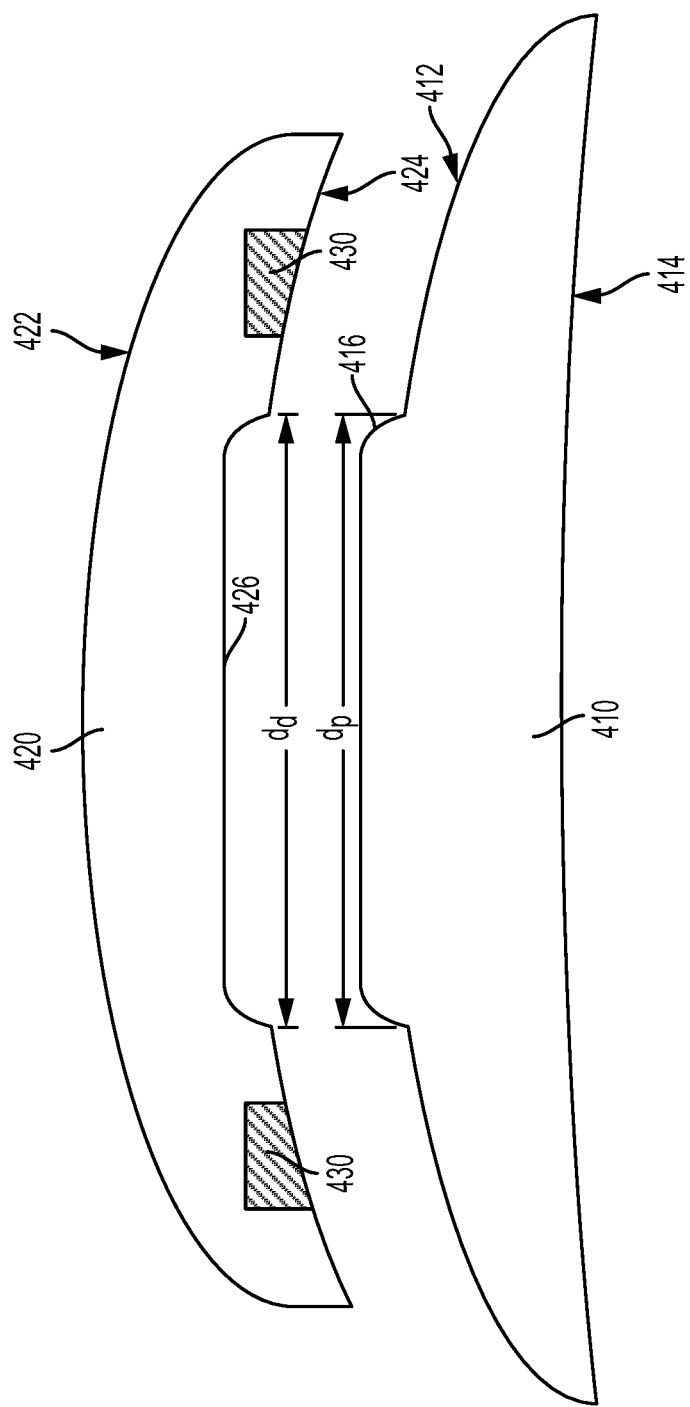
FIGS. 4 and 5 show example lenses usable in an eye-mountable device.
Figure 5:
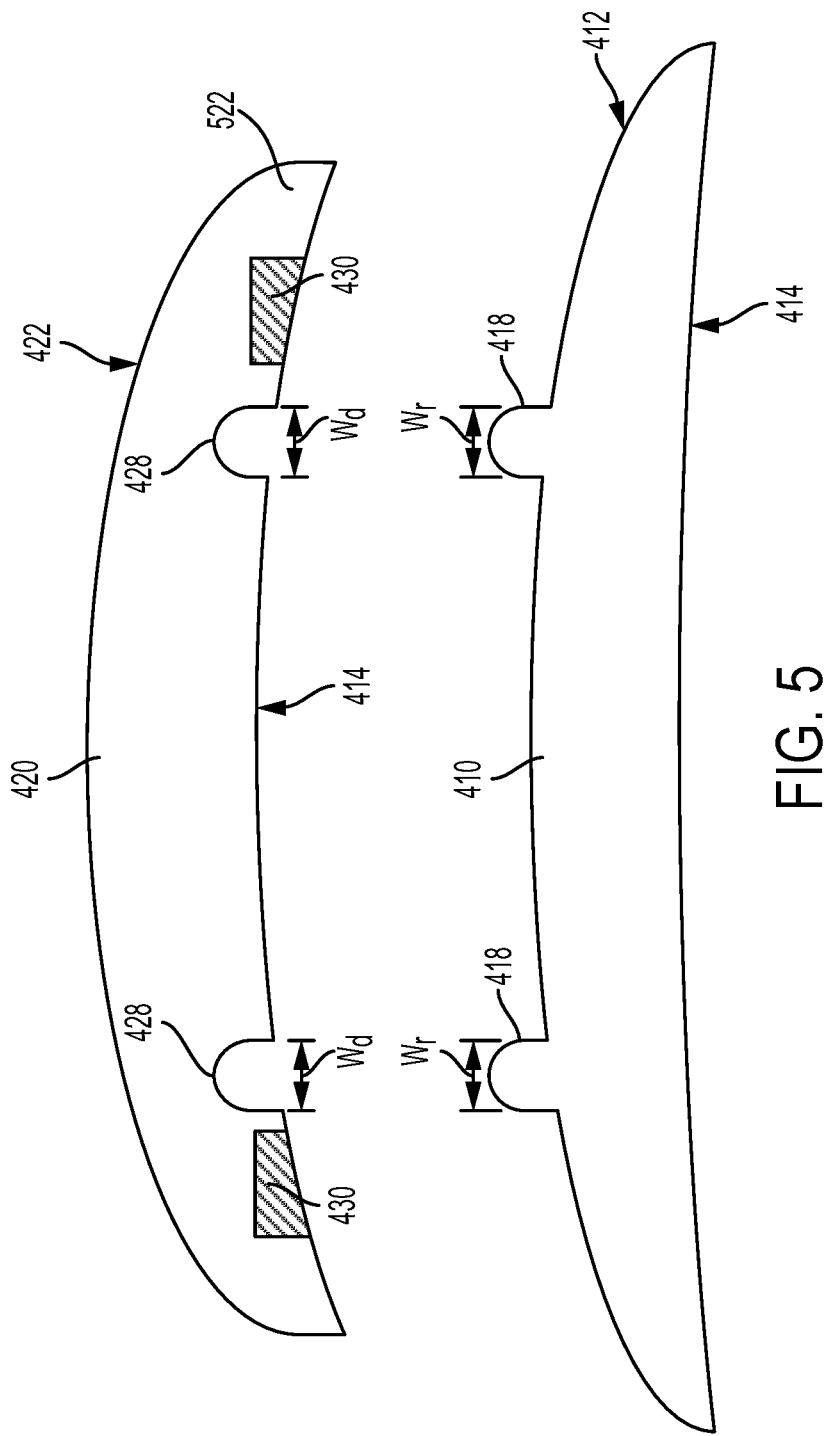

FIGS. 4 and 5 show example cross-sections of lenses that may be formed when performing the steps of blocks 304 and 306 of the method 300. In FIGS. 4 and 5, each of a posterior lens 410 and an anterior lens 420 has an anterior surface 412, 422 and a posterior surface 414, 424. In these examples, the posterior lens 410 may be the first lens, while the anterior lens 420 may be the second lens. As such, an electronic structure 430, which may be the same as or substantially similar to the electronic structure 230 described with respect to FIGS. 2a-2d, may be embedded in the anterior lens 420.

In FIG. 4, the first topographical feature may include a protrusion 416 centrally-located on the anterior surface 412 of the posterior lens 410, and the second topographical feature 426 may include a reciprocally-shaped depression centrally-located the posterior surface 424 of the anterior lens 420. To facilitate mechanical securing the anterior lens 420 to the posterior lens 410, a depression diameter $d_d$ may be the same as or slightly smaller than a protrusion diameter $d_p$. As one example, the depression diameter $d_d$ may be less than or equal to about 5.5 millimeters, and the protrusion diameter $d_p$ may be within several tenths of a millimeter of the depression diameter $d_d$. When the anterior lens 420 is mounted to the posterior lens 410, the protrusion 416 may fit securely in the depression 426, thereby mechanically securing the anterior lens 420 to the posterior lens 410.

FIG. 5 shows an alternative embodiment of the posterior lens 410 and the anterior lens 420. In this example, the first topographical feature includes an annular ring 418 that projects from the anterior surface 412 of the posterior lens 410. A reciprocally-shaped annular depression 428 may be formed in the posterior surface 424 of the anterior lens 420, with a radial width $w_d$ of the annular depression 428 being slightly smaller than a radial width $w_r$ of the annular ring 418. In this example, mounting the anterior lens 420 on the posterior lens 410 may involve aligning the annular depression 428 over the annular ring 418. Applying a compressive force to the anterior lens 420 and the posterior lens 410 may cause the annular ring 428 to interface with the annular depression 428, thereby mechanically securing the anterior lens 420 to the posterior lens 410.

In some embodiments, a different technique could be used to mount the second lens 420 to the first lens 410 in lieu of or in addition to a compressive force. For instance, the anterior lens 420 may be heated (or not allowed to sufficiently cool) prior to mounting the anterior lens 420 on the posterior lens 410. In a heated state, the second topographical feature (e.g., the depression 426 or the annular depression 428) may have about the same diameter or radial width as the first topographical feature (e.g., the protrusion 416 or the annular ring 418). The first topographical feature may interface more easily with second topographical feature than in an example where the posterior lens 410 and the anterior lens 420 have approximately the same temperature, thereby requiring less compressive force to mount the second lens on the first lens. The resulting eye-mountable device may then be cooled, causing the second topographical feature to contract. This contraction may cause the second topographical feature to bind to the first topographical feature, thereby mechanically securing the anterior lens 420 to the posterior lens 410.

While the first topographical feature and the second topographical features are described as being a protrusion and a depression, respectively, in the above examples, the first topographical feature could be a depression in the anterior surface 412 of the posterior lens 410, and the second topographical feature could be a reciprocally-shaped protrusion or projection in the posterior surface 424 of the anterior lens 420. Moreover, depending on the configuration of the electronic structure 430 and the analyte measured by the sensor, the first lens may be the anterior lens and the second lens may be the posterior lens.

While the method 300 has been described thus far in the context of fabricating an eye-mountable device, the method 300 could be adapted for forming a different body-mountable device, such as a skin-mountable device. In such an example, performing the steps of blocks 304 and 306 may respectively result in forming a first polymeric layer and a second polymeric layer, as opposed to the above-described first lens and second lens. Depending on the application, e.g., the analyte measured by the sensor of the electronic structure, the first polymeric layer may be the anterior layer, and the second polymeric layer may be the posterior layer.

Figure 6:
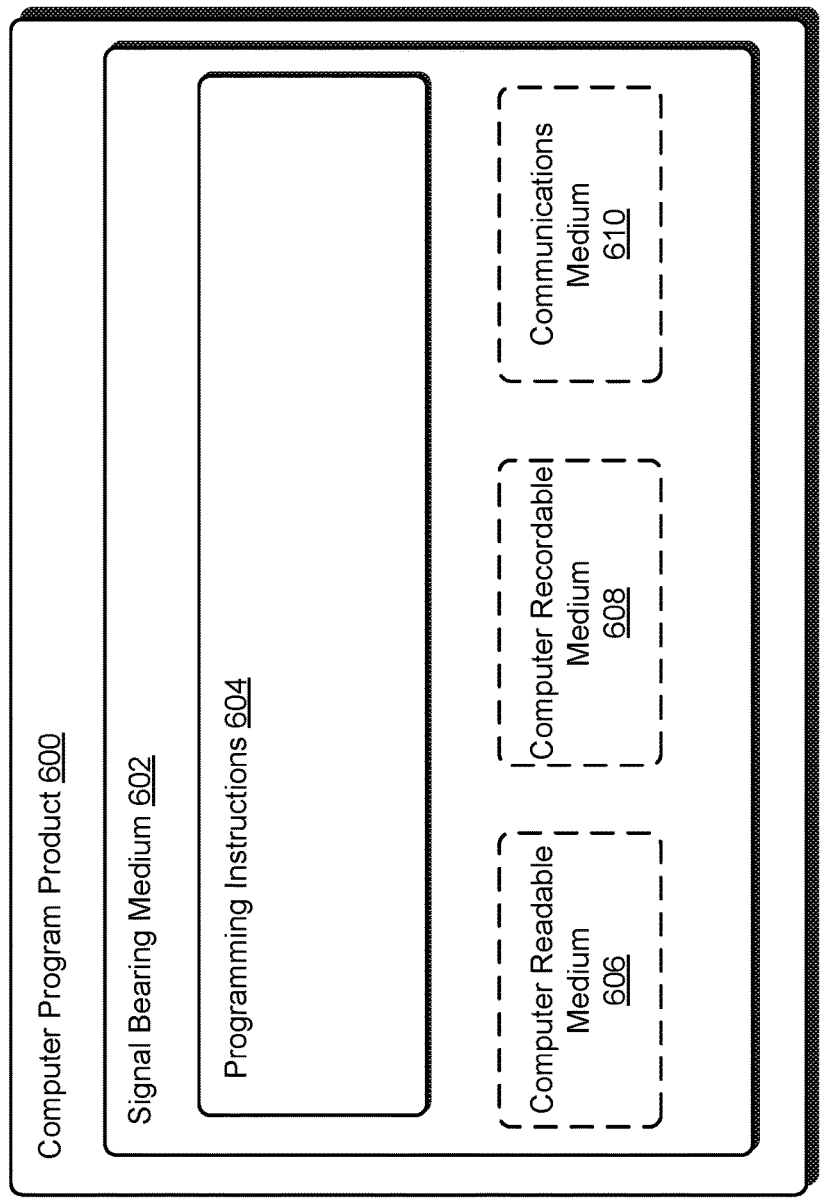
FIG. 6 depicts a computer-readable medium configured according to an example embodiment.

FIG. 6 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause a system to carry out the various functions, tasks, capabilities, etc., described above.

In some embodiments, the disclosed techniques can be implemented by computer program instructions encoded on a non-transitory computer-readable storage media in a machine-readable format, or on other non-transitory media or articles of manufacture. FIG. 6 is a schematic illustrating a conceptual partial view of a computer program product 600 that includes a computer program for executing a computer process on a computing device, to perform any of the methods described herein.

In one embodiment, the computer program product 600 is provided using a signal bearing medium 602. The signal bearing medium 602 may include one or more programming instructions 604 that, when executed by one or more processors may provide functionality or portions of the functionality described above with respect to FIG. 3. In some examples, the signal bearing medium 602 can include a non-transitory computer-readable medium 606, such as, but not limited to, a hard disk drive, a Compact Disc (CD), a Digital Video Disk (DVD), a digital tape, memory, etc. In some implementations, the signal bearing medium 602 can be a computer recordable medium 608, such as, but not limited to, memory, read/write (R/W) CDs, R/W DVDs, etc. In some implementations, the signal bearing medium 602 can be a communications medium 610, such as, but not limited to, a digital and/or an analog communication medium (e.g., a fiber optic cable, a waveguide, a wired communications link, a wireless communication link, etc.). Thus, for example, the signal bearing medium 602 can be conveyed by a wireless form of the communications medium 610.

The one or more programming instructions 604 can be, for example, computer executable and/or logic implemented instructions. In some examples, a computing device is configured to provide various operations, functions, or actions in response to the programming instructions 604 conveyed to the computing device by one or more of the computer readable medium 606, the computer recordable medium 608, and/or the communications medium 610.

The non-transitory computer readable medium 606 can also be distributed among multiple data storage elements, which could be remotely located from each other. The computing device that executes some or all of the stored instructions can be a microfabrication controller, or another computing platform. Alternatively, the computing device that executes some or all of the stored instructions could be remotely located computer system, such as a server.

IV. CONCLUSION

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

We claim:

1. A method comprising:
   forming a first lens that has a first topographical feature;
   forming a second lens that has a second topographical feature, wherein embedded in the second lens is an electronic structure that comprises an antenna, a sensor, and an electronic device, and wherein the first topographical feature and the second topographical feature have reciprocal shapes; and
   mounting the second lens on the first lens such that first topographical feature interfaces with the second topographical feature, thereby mechanically securing the second lens to the first lens.

2. The method of claim 1, wherein the first lens is a posterior lens and the second lens is an anterior lens.

3. The method of claim 1, wherein the first topographical feature comprises a protrusion formed in an anterior side of the first lens, the second topographical feature comprises a cylindrical depression formed in a posterior side of the second lens, and a diameter of the depression is less than or equal to a diameter of the protrusion.

4. The method of claim 1, wherein first topographical feature is an annular ring formed on an anterior side of the first lens, the second topographical feature is an annular depression formed in a posterior side of the second lens, and a radial width of the annular depression is less than or equal to a radial width of the annular ring.

5. The method of claim 1, wherein a material of the first lens comprises a hydrogel and a material of the second lens comprises an elastomer.

6. The method of claim 5, wherein the material of the first lens comprises a silicone hydrogel.

7. The method of claim 5, wherein the material of the second lens comprises a silicone elastomer.

8. The method of claim 1, wherein a material of each of the first lens and the second lens comprises a hydrogel.

9. The method of claim 8, wherein the material of at least one of the first lens or the second lens comprises a silicone hydrogel.

10. The method of claim 1, wherein the first topographical feature is centrally-located on an anterior side of the first lens, and the second topographical feature is centrally-located on a posterior side of the second lens.

11. An eye-mountable device comprising:
    a first lens having a first topographical feature;
    a second lens having a second topographical feature, wherein the first topographical feature and the second topographical feature have reciprocal shapes, and wherein the second lens is mounted on the first lens such that the first topographical features interfaces with the second topographical feature, thereby mechanically securing the second lens to the first lens; and
    an electronic structure comprising an antenna, a sensor, and an electronic device, the electronic device being embedded in the second lens.

12. The eye-mountable device of claim 11, wherein the first lens is a posterior lens and the second lens is an anterior lens.

13. The eye-mountable device of claim 11, wherein the first topographical feature comprises a protrusion formed in an anterior side of the first lens, the second topographical feature comprises a depression formed in a posterior side of the second lens, and a diameter of the depression is less than or equal to a diameter of the protrusion.

14. The eye-mountable device of claim 11, wherein first topographical feature is an annular ring formed on an anterior side of the first lens, the second topographical feature is an annular depression formed in a posterior side of the second lens, and a radial width of the annular depression is less than or equal to a radial width of the annular ring.

15. The eye-mountable device of claim 11, wherein a material of the first lens comprises a hydrogel and a material of the second lens comprises an elastomer.

16. The eye-mountable device of claim 15, wherein the material of the first lens comprises a silicone hydrogel.

17. The eye-mountable device of claim 15, wherein the material of the second lens comprises a silicone elastomer.

18. The eye-mountable device of claim 11, wherein a material of each of the first lens and the second lens comprises a hydrogel.

19. The eye-mountable device of claim 18, wherein the material of at least one of the first lens or the second lens comprises a silicone hydrogel.

20. The eye-mountable device of claim 11, wherein the first topographical feature is centrally-located on an anterior side of the first lens, and the second topographical feature is centrally-located on a posterior side of the second lens.

* * * * *